United States Patent
Leonard et al.

(10) Patent No.: US 6,556,869 B1
(45) Date of Patent: Apr. 29, 2003

(54) ELECTRODE INTRODUCER FOR A PERCUTANEOUS ELECTRICAL THERAPY SYSTEM

(75) Inventors: Paul Leonard, Woodinville, WA (US); Jon M. Bishay, Woodinville, WA (US)

(73) Assignee: Vertis Neuroscience, Inc., Seattle, WA (US)

(*) Notice: Subject to any disclaimer, the term of this patent is extended or adjusted under 35 U.S.C. 154(b) by 0 days.

(21) Appl. No.: 09/451,799

(22) Filed: Dec. 1, 1999

(51) Int. Cl.[7] ................................. A61N 1/18
(52) U.S. Cl. .................. 607/46; 607/115; 128/907; 128/DIG. 26
(58) Field of Search ................. 607/115, 145, 607/148, 149, 146; 600/382, 386, 372, 548; 128/907, DIG. 26

(56) References Cited

U.S. PATENT DOCUMENTS

| | | | |
|---|---|---|---|
| 3,030,959 A | 4/1962 | Grunert | 606/182 |
| 3,090,151 A | 5/1963 | Stewart et al. | 43/6 |
| 3,208,452 A | 9/1965 | Stern | 606/182 |
| 3,938,526 A | 2/1976 | Anderson et al. | 606/189 |
| 3,943,935 A | 3/1976 | Cameron | 606/188 |
| 3,983,881 A | 10/1976 | Wickham | 607/43 |
| 4,139,011 A * | 2/1979 | Benoit et al. | 128/329 R |
| 4,153,059 A | 5/1979 | Fravel et al. | 607/41 |
| 4,207,903 A | 6/1980 | O'Neill | 607/131 |
| 4,256,116 A | 3/1981 | Meretsky et al. | 607/46 |
| 4,262,672 A | 4/1981 | Kief | 606/189 |
| 4,281,659 A | 8/1981 | Farrar et al. | 600/351 |
| 4,284,856 A | 8/1981 | Hochmair et al. | 607/9 |
| 4,381,012 A | 4/1983 | Russek | 600/383 |
| 4,408,617 A | 10/1983 | Auguste | 600/548 |
| 4,431,000 A | 2/1984 | Butler et al. | 607/73 |
| 4,437,467 A | 3/1984 | Helfer et al. | 600/377 |
| 4,512,351 A | 4/1985 | Pohndorf | 607/117 |
| 4,541,432 A | 9/1985 | Molina-Negro et al. | 607/46 |
| 4,556,064 A | 12/1985 | Pomeranz et al. | 607/66 |
| 4,583,549 A | 4/1986 | Manoli | 600/391 |
| 4,685,466 A | 8/1987 | Rau | 600/387 |
| 4,686,996 A | 8/1987 | Ulbrich | 600/377 |
| 4,712,558 A | 12/1987 | Kidd et al. | 607/48 |
| D297,047 S | 8/1988 | Hon et al. | D24/187 |
| 4,765,310 A | 8/1988 | Deagle et al. | 600/14 |
| 4,895,154 A | 1/1990 | Bartelt et al. | 607/50 |
| 4,934,371 A | 6/1990 | Malis et al. | 600/386 |
| 4,949,734 A | 8/1990 | Bernstein | 128/897 |
| 4,953,564 A | 9/1990 | Berthelsen | 607/120 |
| 4,979,508 A | 12/1990 | Beck | 607/54 |
| 5,012,811 A | 5/1991 | Malis et al. | 600/376 |

(List continued on next page.)

FOREIGN PATENT DOCUMENTS

| | | | | |
|---|---|---|---|---|
| FR | 2 500 309 | 8/1982 | | A61N/1/32 |
| FR | 2500745 | 9/1982 | | A61N/1/36 |
| GB | 2 163 355 A | 7/1985 | | A61N/1/05 |
| GB | 2 255 719 A | 5/1991 | | A61N/1/32 |

OTHER PUBLICATIONS

Ahmed et al., "Percutaneous Electrical Nerve Stimulation (PENS): A Complementary Therapy for the Management of Pain Secondary to Bony Metastasis," Clinical Journal of Pain 14:320–3 (1998).

(List continued on next page.)

*Primary Examiner*—Carl Layno
(74) *Attorney, Agent, or Firm*—Perkins Coie LLP

(57) ABSTRACT

A percutaneous electrode introducer, such as for use with a percutaneous electrical therapy system. In a preferred embodiment, the percutaneous electrode introducer includes a housing adapted to be held in a user's hand, the housing having an aperture at a distal end; an electrode disposed in the housing, the electrode having a sharp point at a distal end; and an actuator adapted to be operable by a user to move the electrode through the aperture and completely out of the housing to place the sharp point of the electrode beneath a patient's skin.

9 Claims, 5 Drawing Sheets

U.S. PATENT DOCUMENTS

| | | | | |
|---|---|---|---|---|
| D318,330 | S | 7/1991 | Doty et al. | D24/187 |
| 5,036,850 | A | 8/1991 | Owens | 607/66 |
| 5,054,486 | A | 10/1991 | Yamada | 607/3 |
| 5,094,242 | A | 3/1992 | Gleason et al. | 600/377 |
| 5,117,826 | A | 6/1992 | Bartelt et al. | 607/46 |
| 5,211,175 | A | 5/1993 | Gleason et al. | 600/548 |
| 5,246,014 | A | 9/1993 | Williams et al. | 607/122 |
| 5,255,691 | A | 12/1993 | Otten | 607/117 |
| 5,269,304 | A | 12/1993 | Matthews | 607/46 |
| 5,281,218 | A | 1/1994 | Imran | 606/41 |
| 5,332,401 | A | 7/1994 | Davey et al. | 607/116 |
| D357,069 | S | 4/1995 | Plahn et al. | D24/187 |
| 5,417,719 | A | 5/1995 | Hull et al. | 607/46 |
| 5,423,314 | A | 6/1995 | Schmid | 600/376 |
| 5,439,440 | A | 8/1995 | Hofmann | 604/20 |
| 5,449,378 | A | 9/1995 | Schouenborg | 607/46 |
| 5,593,429 | A | 1/1997 | Ruff | 607/116 |
| 5,649,936 | A | 7/1997 | Real | 606/130 |
| 5,682,233 | A | 10/1997 | Brinda | 356/246 |
| 5,702,359 | A | 12/1997 | Hofmann et al. | 604/20 |
| 5,810,762 | A | 9/1998 | Hofmann | 604/20 |
| 5,851,223 | A | 12/1998 | Liss et al. | 607/46 |
| 5,861,015 | A | 1/1999 | Benja-Athon | 607/46 |
| 5,873,849 | A | 2/1999 | Bernard | 604/20 |
| 5,928,144 | A | 7/1999 | Real | 600/378 |
| 5,941,845 | A | 8/1999 | Tu et al. | 604/53 |
| 5,948,008 | A | 9/1999 | Daikuzono | 607/89 |
| 5,968,011 | A | 10/1999 | Larsen et al. | 604/93 |
| 5,968,063 | A | * 10/1999 | Chu et al. | 606/185 |
| 6,009,347 | A | 12/1999 | Hofmann | 604/21 |
| 6,032,064 | A | 2/2000 | Devlin et al. | 600/383 |
| 6,035,236 | A | 3/2000 | Jarding et al. | 607/53 |
| 6,050,992 | A | 4/2000 | Nichols | 606/41 |
| 6,068,650 | A | 5/2000 | Hofmann et al. | 607/2 |
| 6,117,077 | A | 9/2000 | Del Mar et al. | 600/301 |
| 6,122,547 | A | 9/2000 | Benja-Athon | 607/46 |
| 6,208,893 | B1 | 3/2001 | Hofmann | 604/21 |
| 6,219,569 | B1 | 4/2001 | Kelly et al. | 600/386 |
| D443,063 | S | 5/2001 | Pisani et al. | D24/187 |
| 6,269,270 | B1 | 7/2001 | Boveja | 607/45 |
| 6,304,785 | B1 | 10/2001 | McCreery et al. | 607/116 |
| 6,341,237 | B1 | 1/2002 | Hurtado | 607/148 |
| 6,355,021 | B1 | 3/2002 | Nielsen et al. | 604/263 |

OTHER PUBLICATIONS

Ahmed et al., "Percutaneous Electrical Nerve Stimulation: An Alternative to Antiviral Drugs for Herpes Zoster," Anesth. Analg. 87:911–4 (1998).

Ballegaard et al., "Acupuncture and Transcutaneous Electric Nerve Stimulation in the Treatment of Pain Associated with Chronic Pancreatitis," Scan.J.Rehab.Med. 20:1249–54 (1985).

Balogun et al., "The effects of acupuncture, electroneedling and transcutaneous electrical stimulation therapies on peripheral haemodynamic functioning,"Disability and Rehab. 20:41–8 (1998).

Bushnell et al., "Electrical stimulation of peripheral and central pathways for the relief of musculoskeletal pain," Can.J.Physiol.Pharmacol. 69:697–703 (1991).

Cheng et al., "Electrotherapy of Chronic Musculoskeletal Pain: Comparison of Electroacupuncture and Acupuncture-Like Transcutaneous Electrical Nerve Stimulation," Clin.J-.Pain 2:143–9 (1987).

Cheng et al., "Electroacupuncture analgesia could be mediated by at least two pain–relieving mechanisms: endorphin and non–endorphin systems," Life Sciences 25:1957–62 (1979).

Cheng et al., "Electroacupuncture elevates blood cortisol levels in naïve horses; sham treatment has no effect," Intern.J.Neuroscience 10:95–7 (1980).

Gadsby et al., "Nerve stimulation for low back pain —a review," Nursing Standard 11:32–3 (1997).

Ghoname et al., "Percutaneous electrical nerve stimulation: an alternative to TENS in the management of sciatica," Pain 83:193–9 (1999).

Ghoname et al., "Percutaneous Electrical Nerve Stimulation for Low Back Pain," JAMA 281:818–23 (1999).

Ghoname et al., "The Effect of Stimulus Frequency on the Analgesic Response to Percutaneous Electrical Nerve Stimulation in Patients with Chronic Low Back Pain," Anesth.Analg. 88:841–6 (1999).

Ghoname et al., "The effect of the duration of electrical stimulation on the analgesic response," Anesth.Analg. 88:S211 (1999).

Landau et al., "Neuromodulation Techniques for Medically Refractory Chronic Pain," Annu.Rev.Med. 44:279–87 (1993).

Lehmann et al., "Efficacy of Electroacupuncture and TENS in the Rehabilitation of Chronic Low Back Pain Patients," Pain 26:277–90 (1986).

Omura, "Basic electrical parameters for safe and effective electro–therapeutics [electroacupuncture, TES,TENMS (or TEMS), TENS and electro–magnetic field stimulation with or without drug field] for pain, neuromuscular skeletal problems, and circulatory disturbances," Acupuncture & Electro–Therapeutics Res. 12:201–25 (1987).

Omura, "Electrical parameters for safe and effective electro–acupuncture and transcutaneous electrical stimulation: Threshold potentials for tingling, muscle contraction and pain; and how to prevent adverse effects of electro–therapy," Acupuncture & Electro–Therapeutics Res. 10:335–7 (1985).

Romita et al., "Parametric Studies on Electroacupuncture-Like Stimulation in a Rat Model: Effects of Intensity, Frequency, and Duration of Stimulation on Evoked Antinociception," Brain Res.Bull. 42:289–96 (1997).

Ulett et al., "Electroacupuncture: Mechanisms and Clinical Application," Biol.Psych. 44:129–38 (1998).

Radionics RFG–3C product brochure (1997).

Rehabilicare Ortho Dx product brochure.

Rehabilicare SporTX product brochure.

AAMI Neurosurgery Committee; AAMI Implantable Neurostimulator Subcommittee. Implantable peripheral nerve stimulators. Assoc. for the Advancement of Medical Instrumentation (1995) NS15–1995, cover–8, 11 pages.**

Almay, B.G.L. et al., "Long–Term High Frequency Transcutaneous Electrical Nerve Stimulation (hi–TNS) in Chronic Pain. Clinical Response and Effects of CSF–Endorphins, Monoamine Metabolites, Substance P–Like Immunoreactivity (SPLI) and Pain Measures", J. Physchosom. Res. (1985) 29:247–257, 11 pages.

Baker, L. et al., "Effects of Waveform on Comfort During Neuromuscular Electrical Stimulation", Clinical Orthopedics and Related Research (Aug. 1988) 233:75–85.

Balogun, J., "Effects of Ramp Time on Sensory, Motor and Tolerance Thresholds During Exogenous Electrical Stimulation", The Journal of Sports Medicine and Physical Fitness (Dec. 1991) 3:4, 521–526.

BD Safety Products. BD Vacutainer Safety–Lok Blook Collection Set; BD Vacutainer SafetyGlide Blood Collection Assembly and BD Vacutainer Eclipse Blood Collection Needle, 1 page.

BD Safety Flow Lancet –Product Number 366356. BD catalog 1997–2000, Capillary Access, http://catalog.bd.com/scripts/OBDsheet.exe?FNC=productlist_Alistproducts_html_366356 (Aug. 7, 2001) (3 pages).

BD Vacutainer SafetyGlide Blood Collection Assembly. Quick Reference Card (1999), 1 page.

Brull, S., Silverman, D.G., "Pulse Width, Stimulus Intensity, Electrode Placement, and Polarity During Assessment of Neuromuscular Block", Anesthesiology (Oct. 1995) 83:702–709.

Carroll, D., "Randomization is Important in Studies with Pain Outcomes: Systematic Review of Transcutaneous Electrical Nerve Stimulation in Acute Postoperative Pain", Br J Anaesth. (1996) 77:798–803**.

Cassuto, J. et al., "The Use of Modulated Energy Carried on a High Frequency Wave for the Relief of Intractable Pain", Int.J.Clin. Pharm.Res. (1993) XIII(4) 239–241**.

Cramp AF et al., "The Effect of High and Low Frequency Transcutaneous Electrical Nerve Stimulation Upon Cutaneous Blood Flow and Skin Temperature in Healthy Subjects", Clin.Physio. (2000) 20:150–7.

Eclipse+ Dual Channel Trancutaneous Electrical Nerve Stimulator User's Manual (1993), 31 pages.**

Electrotherapy for Rehabilitation, Empi Cervical Traction, http://www.empi.com/b/b2.htm, Oct. 22, 2001, 3 pages.

Epix XL Tens Instruction Manual, Empi, Inc. (1988), 21 pages**.

Foster, N. et al., Manipulation of Transcutaneous Electrical Nerve Stimulation Variables Has No Effect on Two Models of Experimental Pain in Humans, The Clinical Journal of Pain (1996) 12:301–310**.

Galletti S.P. et al., Highlights concerning low frequencyhigh intensity TENS (review). Minerva Stomatol (1995) 44:421–9**.

Ghoname et al., "Does the Stimulus Frequency Affect the Analgesic Response to Electrical Stimulation?", Anesth. Analg. (1999) 88:S210, 1 page.

Gopalkrishnann, P., Sluka, K.A., "Effect of Varying Frequency, Intensity, and Pulse Duration of Transcutaneous Electrical Nerve Stimulation on Primary Hyperalgesia in Inflamed Rats", Arch.,Phys.Med.Rehabil. (Jul. 2000) 81:984–990.

Gracanin, F., Trnkoczy, A. "Optimal Stimulus Parameters for Minimum Pain in the Chronic Stimulation of Innervated Muscle"Arch.Phys.Med. Rehabil. (Jun. 1975) 56:243–249.

Hamza, M.A. et al., "Effect of the Duration of Electrical Stimulation on the Analgesic Response in Patients with Low Back Pain", Anesthesiology (Dec. 1999), V. 91, No. 6:1622–7.

Hamza Ma et al., "Effect of the frequency of transcutaneous electrical nerve stimulation on the postoperative opioid analgesic requirement and recovery profile", Anesthesiology (Nov. 1999) 91:1232–8.

Han JS et al., "Effect of Low and High–Frequency TENS on Met–enkephalin–Arg–Phe and Dynorphin A Immunoreactivity in Human Lumbar CSF", Pain (1991) 47:295–8**.

Healthronics Hans LY257 User Manual, 15 pages.

Innovative Healthcare: Electrotherapy Pain & Rehabilitation Product Solutions from Rehabilicare. [Includes product description of SporTX and Ortho DX]. 1999, 3 pages, http://www.mvpdesign.com/sites/rehavilicare/all products.html.

Instruction Manual for the Empi Epix VT Tens Device, 1997, Dual Channel Transcutaneous Electrical Nerve Stimulator, Empi, Inc., 29 pages.**

Intelect Legend Stim Clinical Reference Manual, vol. 4 Intelect Legend Series, Chattanooga Group, Inc., 31 pages.

Jette, D., "Effect of Different Forms of Transcutaneous Electrical Nerve Stimulation on Experimental Pain", Physical Therapy (Feb. 1986) 66:2, 187–193.

Johnson, M.I., "Analgesic Effects of Different Pulse Patterns of Trancutaneous Electrical Nerve Stimulation on Cold–induced Pain in Normal Subjects", Journal of Psychosomatic Research (1991) 35:2–3; 313–321.

Johnson, Mi, "Analgesic Effects of Different Frequencies of Transcutaneous Electrical Nerve Stimulation on Cold–Induced Pain in Normal Subjects", Pain (1989) 39:231–6**.

Johnson, Mi, et al. "An In–Depth Study of Long Term Users of Transcutaneous Electrical Nerve Stimulation (TENS). Implications for Clinical Use of TENS", Pain (1991) 44:221–9**.

Katims, J.J. et al., "Transcutaneous Nerve Stimulation. Frequency and Waveform Specificity in Humans", Appl. Neurophysiol (1986 49:86–91**.

Leem, J., "Electrophysiological evidence for the antinociceptive effect of transcutaneous electrical stitmulation on mechanically evoked responsiveness of dorsal horn neurons in neuropathic rats", Neuroscience letters(1995) 192:197–200**.

Liss S., Liss B., "Physiological and Therapeutic Effects of High Frequency Electrical Pulses", Integr.Physio.Behav. Sci (Apr.–Jun. 1996) 31:88–94.

Model AWQ–104B Multi–Purpose Electronic Acupunctoscope Instruction Manual, 10 pages.

Marchand, S., et al., "Modulation of Heat Pain Perception by High Frequency Transcutaneous Electrical Nerve Stimulation (TENS)", Clin.J.Pain (1991) 7:122–9**.

Moreno–Aranda J., "Electrical Parameters for over–theskin muscle stimulation", J. Biomechanics (1981) 14:9, 579–585**.

Moreno–Aranda J., Seireg, A., "Investigation of over–the-skin electrical stimulation parameters for different normal muscles and subjects", J. Biomechanics (1981) 14:9; 587–593**.

O'Brien, WJ, "Effect of Transcutaneous Electrical Nerve Stimulation on Human Blood B–Endorphin Level", Physical Therapy (Sep. 1984) 64:1367–1374.

Ordog, G., "Transcutaneous Electrical Nerve Stimulation Versus Oral Analgesic: A Randomized Double–Blind Controlled Study in Acute Traumatic Pain", American Journal of Emergency Medicine (Jan. 1987) 5:1, 6–10.

Ortho DX Product Data Sheet.

Pointer F–3 Instruction Manual, Ito Co, Ltd., 10 pages.

Rooney, J.G., et al., "Effect of Variation in the Burst and Carrier Frequency Modes of Neuromuscular Electrical Stimulation on Pain Perception of Healthy Subjects", Phys. Ther. (Nov. 1992) 72:11, 800–808.

Sluka, K.A., "Treatment with Either High or Low Frequency TENS Reduced the Secondary Hyperalgesia Observed After Injection of Kaolin andn Carrageenan into the Knee Joint", Pain (1998) 77:97–102.

SMP–plus. The Pain Relief Solution for Hard to Treat Patients, Rehabilicare (2 pages).

Somers, D.L., "High–Frequency Transcutaneous Electrical Nerve Stimulation Alters Thermal but not Mechanial Allodynia Following Chronic Constriction Injury of the Rat Sciatic Nerve", Arch. Phys. Med. Rehabil. (Nov. 1998) 79:1370–6.

Sportx Product Data Sheet.

Starobinets, M., Volkova, L., [Analgesic Effect of High–Frequency and Acupuncture–Like Trancutaneous Electric Stimulation of Nerve Fibers in Spinal Osteochondritis]. Zh Nevropatol Psikhiatr Im S.S. Korsakova (1985) 85–350–4 **

Van Doren, CL, "Contours of Equal Perceived Amplitude and Equal Perceived Frequency for Electrocutaneous Stimuli", Percept.Phychophys. (1977) 59:613–22**.

White, P.F. et al., "Percutaneous Neuromodulation Therapy: Does the Location of Electrical Stimulation Effect the Acute Analgesic Response?", Anesth. Analg. (2000) 91:1–6.

White, P.F. et al., "The Effect of Montage on the Analgesic Response to Percutaneous Neuromodulation Therapy", Anesth. Analg. (2001) 92:483–7.

U.S. patent application Ser. No. 09/452,477, entitled "Percutaneous Electrical Therapy System With Electrode Entry Angle Control," Filed on Dec. 1, 1999, Attorney Docket No. 33734800US.

U.S. patent application Ser. No. 09/452,663, entitled "Percutaneous Electrical Therapy System Providing Electrode Axial Support," filed on Dec. 1, 1999, Attorney Docket No. 337348005US.

U.S. patent application Ser. No. 09/452,508, entitled "Percutaneous Electrical Therapy System With Electrode Depth Control," filed on Dec. 1, 1999, Attorney Docket No. 337348006US.

U.S. patent application Ser. No. 09/451795 entitled "Percutaneous Electrical Therapy System With Position Maintenance," filed on Dec. 1, 1999, Attorney Docket No. 337348007US.

U.S. patent application Ser. No. 09/452,510, entitled "Percutaneous Electrical Therapy System For Minimizing Electrode Insertion Discomfort," filed on Dec. 1, 1999, Attorney Docket No. 337348009US.

U.S. patent application Ser. No. 09/451/800, entitled "Electrode Assembly For a Percutaneous Electrical Therapy System," filed on Dec. 1, 1999, Attorney Docket No. 337348010US.

U.S. patent application Ser. No. 09/451,796, entitled "Electrode Remover For a Percutaneous Electrical Therapy System," filed on Dec. 1, 1999, Attorney Docket No. 337348011US.

U.S. patent application Ser. No. 09/451,547, entitled "Percutaneous Electrical Therapy System With Sharp Point Protection," filed on Dec. 1, 1999, Attorney Docket No. 337348012US.

PCT International Search Report for International Application No. PCT/US01/31441; mailed May 7, 2002; Applicant: Vertis Neuroscience, Inc., 8 pages.

* cited by examiner

ELECTRODE INTRODUCER FOR A PERCUTANEOUS ELECTRICAL THERAPY SYSTEM

BACKGROUND OF THE INVENTION

This invention relates generally to percutaneous electrical therapy systems for medical use. In particular, the invention relates to an electrode introducer for inserting percutaneous electrodes.

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. The efficacy of TENS systems in alleviating pain is questionable at best, however.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," JAMA 281:818–23 (1999); Ghoname et al., "The Effect of Stimulus Frequency on the Analgesic Response to Percutaneous Electrical Nerve Stimulation in Patients with Chronic Low Back Pain," Anesth. Analg. 88:841–6 (1999); Ahmed et al., "Percutaneous Electrical Nerve Stimulation (PENS): A Complementary Therapy for the Management of Pain Secondary to Bony Metastasis," Clinical Journal of Pain 14:320–3 (1998); and Ahmed et al., "Percutaneous Electrical Nerve Stimulation: An Alternative to Antiviral Drugs for Herpes Zoster," Anesth. Analg. 87:911–4 (1998). The contents of these references are incorporated herein by reference.

Thus far, PNT practitioners have used percutaneously placed acupuncture needles attached to waveform generators via cables and alligator clips to deliver the therapy to the patient. This arrangement and design of electrodes and generator is far from optimal. For example, insertion of percutaneous electrodes has thus far been cumbersome and inaccurate. It is therefore an object of this invention to provide an improved percutaneous electrode introducer.

It is a further object of this invention to provide a percutaneous electrical therapy system having electrodes and electrode assemblies that are safe, efficacious, inexpensive and easy to use.

Other objects of the invention will be apparent from the description of the preferred embodiments.

SUMMARY OF THE INVENTION

The invention is a percutaneous electrode introducer, such as for use with a percutaneous electrical therapy system. In a preferred embodiment, the percutaneous electrode introducer includes a housing adapted to be held in a user's hand, the housing having an aperture at a distal end; an electrode disposed in the housing, the electrode having a sharp point at a distal end; and an actuator adapted to be operable by a user to move the electrode through the aperture and completely out of the housing to place the sharp point of the electrode beneath a patient's skin.

In some embodiments, the electrode may have an electrical connector portion at a proximal end, the actuator being further adapted to place the sharp point of the electrode beneath the patient's skin with the electrical connector portion of the electrode being exposed above the patient's skin.

In some embodiments, the actuator is further adapted to be operated by a user's thumb to move the electrode through the aperture.

In some embodiments of the invention, the introducer also has a transmission assembly adapted to move the electrode's sharp point a first distance when the actuator is moved a second distance, the second distance being less than the first distance.

In one particular embodiment, the introducer has a plurality of electrodes, the actuator being operable by the user to move each of the plurality of electrodes individually through the aperture and completely out of the housing to place the sharp point of each electrode beneath a patient's skin. This embodiment may have a magazine in which the plurality of electrodes is disposed, and the magazine may have a plurality of electrode chambers.

In some embodiments, the introducer's aperture is adapted to cooperate with an alignment element to align the introducer with an electrode insertion site.

In some embodiments, the introducer's actuator and electrode are adapted to move in the same direction during placement of the sharp point of the electrode beneath the patient's skin.

In some embodiments, wherein the introducer has a longitudinal axis, the actuator and the electrode being adapted to move along, or parallel to, the longitudinal axis during placement of the sharp point of the electrode beneath the patient's skin.

The invention is described in further detail below with reference to the drawings.

DETAILED DESCRIPTION OF THE PREFERRED EMBODIMENTS

Figure 1:
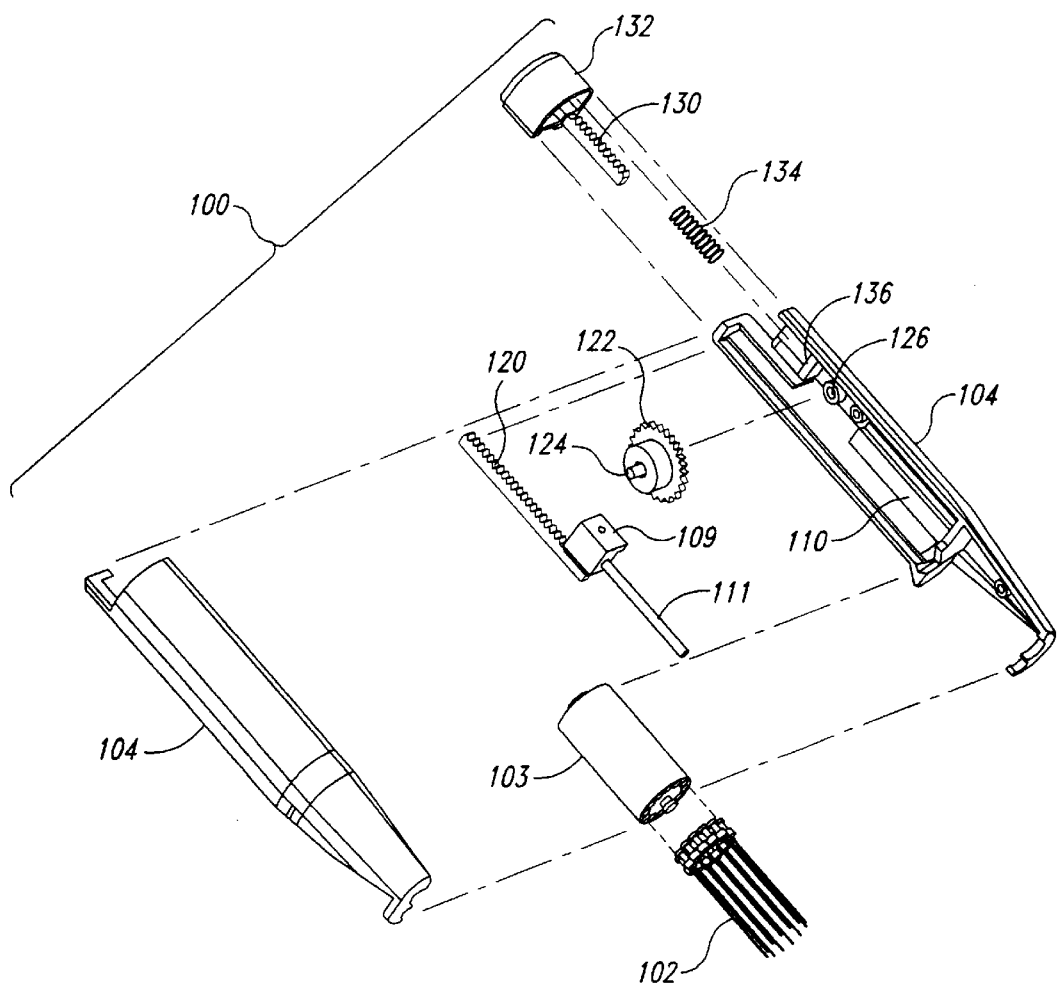
FIG. 1 is an exploded view of an electrode introducer and sharp point protection assembly of yet another embodiment of this invention.

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point to facilitate insertion through the patient's skin and to enhance local current density during treatment. The depth and location of the electrode's point is critical to the therapy. This invention therefore provides a percutaneous electrode introducer that is accurate and easy to use.

As shown in FIGS. 1–4 and 7–9, introducer 100 is designed to insert multiple electrodes. It should be understood that the principles of this invention could be applied to an introducer designed to hold and insert any number of electrodes.

Twelve electrodes 102 are disposed within a magazine 103 rotatably mounted within a housing 104. In this embodiment, housing 104 is a two-part injection molded polystyrene assembly. As seen best in FIG. 2, magazine 103 rotates about a hub 105 mounted on supports formed in housing 104. A leaf spring 106 mates with one of twelve radial grooves 108 formed in magazine 103 to form a twelve-position ratchet mechanism for rotatable magazine 103 in housing 104.

Figure 2:
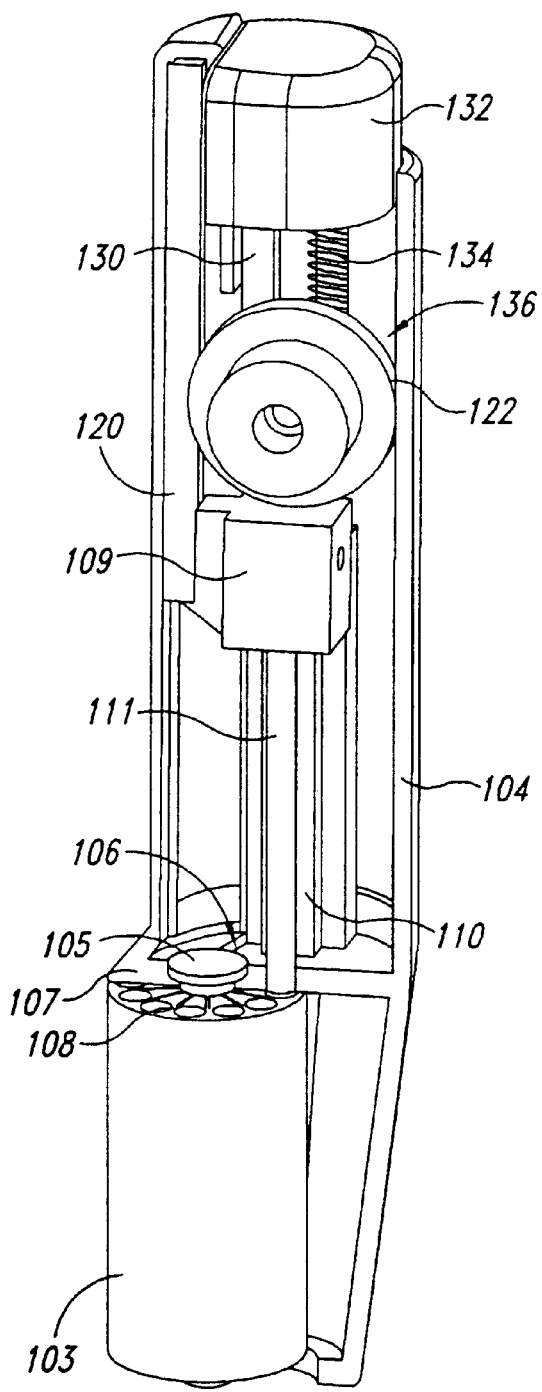
FIG. 2 is a partial sectional view of the introducer and sharp point protection assembly of FIG. 1.
Figure 3:
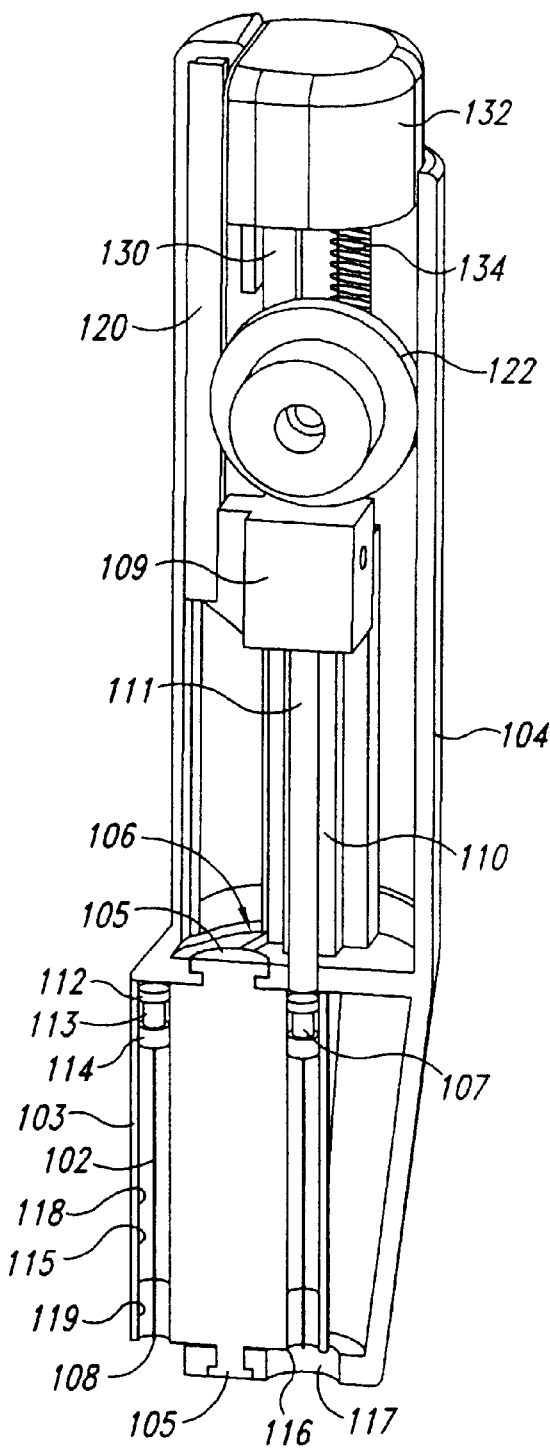
FIG. 3 is a sectional view of the introducer and sharp point protection assembly of FIG. 1.
Figure 4:
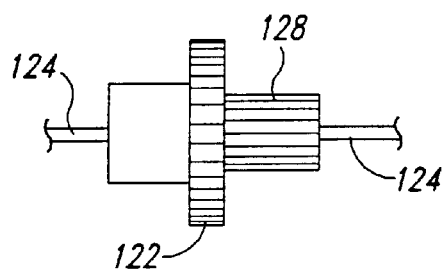
FIG. 4 is an elevational view of gear assemblies of the introducer and sharp point protection assembly of FIG. 1.

Magazine 103 has twelve electrode chambers 115 arranged radially about hub 105. When introducer 100 is completely full, each chamber 115 contains one electrode 102. The diameter of upper portion 118 of chamber 115 is sized to form an interference fit with the wider portions 112 and 114 of electrode handle portion 107 of electrode 102. Lower wide portion 114 of electrode 102 is formed from a compressible material. The diameter of lower portion 119 of chamber 115 is slightly larger so that there is no interference fit between chamber portion 119 and electrode handle 107, for reasons explained below. Each time leaf spring 106 is within a groove 108, the opening 106 of a magazine chamber 115 is lined up with the aperture 117 of introducer 100, as shown in FIGS. 2 and 3.

A slide member 109 is disposed on a rail 110 formed in housing 104. Extending longitudinally downward from slide member 109 is a drive rod 111, and extending longitudinally upward from slide member 109 is a gear rack 120. The teeth of gear rack 120 cooperate with teeth on a rotational gear 122 mounted about a shaft 124 extending into a shaft mount 126 formed in housing 104. A second set of teeth are mounted on a smaller diameter rotational gear 128 (shown more clearly in FIG. 4) which is also mounted about shaft 124. Gears 122 and 128 rotate together about shaft 124.

The teeth of smaller diameter gear 128 mesh with the teeth of a second gear rack 130 extending from a longitudinally-movable actuator 132. A spring 134 mounted between actuator 132 and a spring platform 136 biases actuator 132 away from housing 104. Actuator 132, gears 122 and 128, gear racks 120 and 130, slide member 109 and drive rod 111 form the introducer's transmission assembly.

Figure 5:
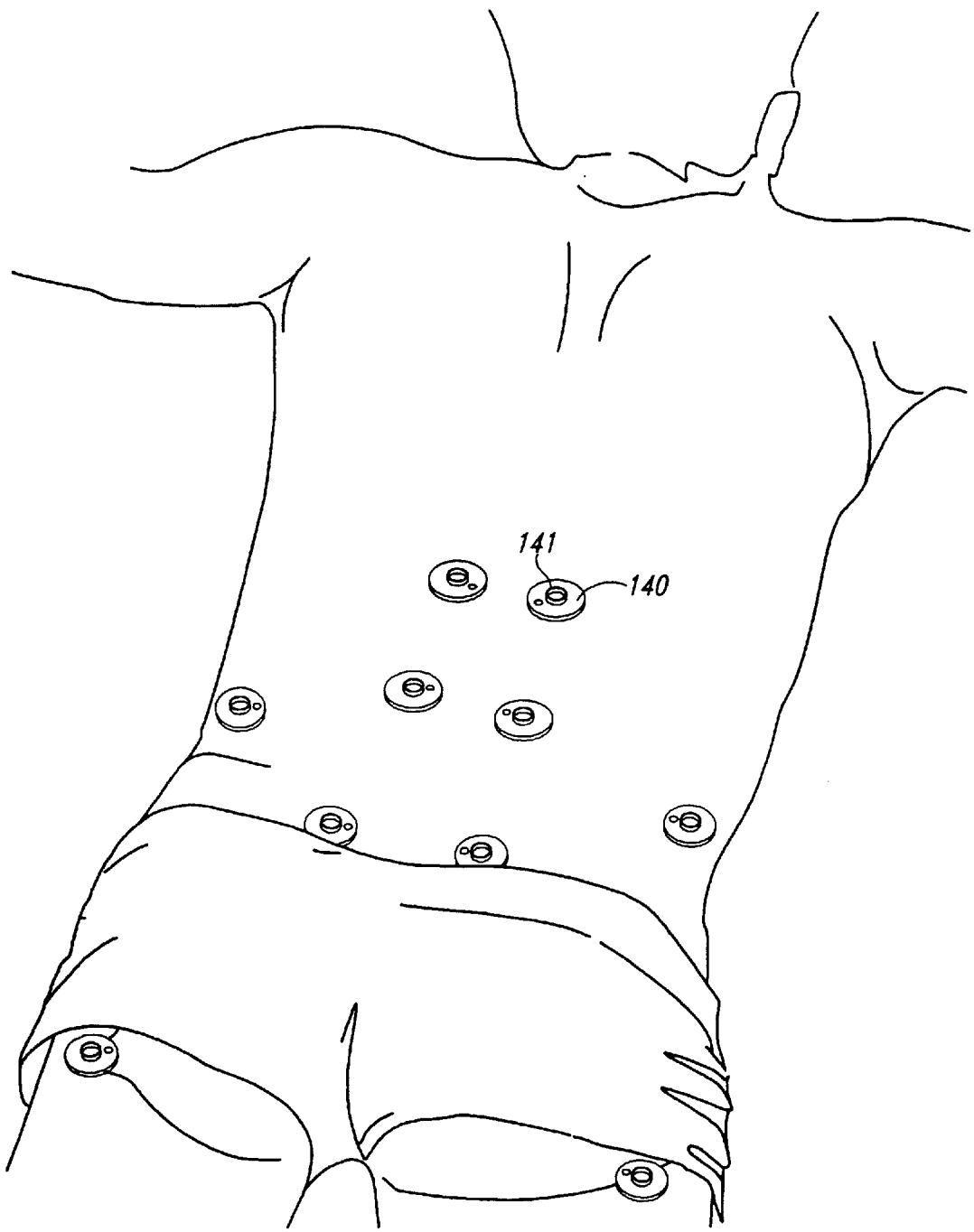
FIG. 5 shows part of the electrode assembly of the embodiment of FIGS. 1–4 in a montage used for treating low back pain using PNT.
Figure 9:
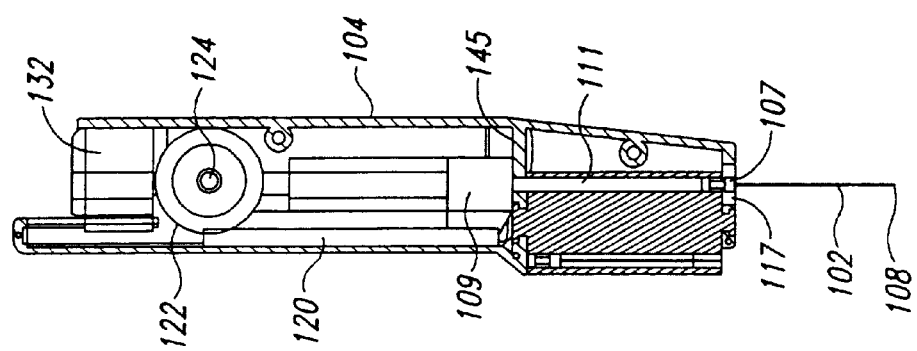
FIG. 9 is a sectional view showing the introducer of FIG. 1 in the process of deploying an electrode, also during insertion of the electrode.

To deploy the electrode assembly of this embodiment, a flexible and compressible annular patch 140 is placed on the patient's skin at the desired site, preferably with adhesive (not shown). For example, to treat low back pain using PNT, the arrangement or montage shown in FIG. 5 may be used. In this montage, five electrodes serve as cathodes and five serve as anodes.

As shown in FIGS. 19 and 20, patch 140 has an annular rigid member 141 disposed in its center and extending upwardly from it. Rigid member 141 has a smaller diameter opening 142 leading to a larger diameter opening 144. The diameter of opening 142 is slightly smaller than the lower wide portion 114 of the handle portion 107 of electrode 102 and slightly larger than the diameter of the central portion 113 of handle portion 107 of electrode 102.

Figure 6:
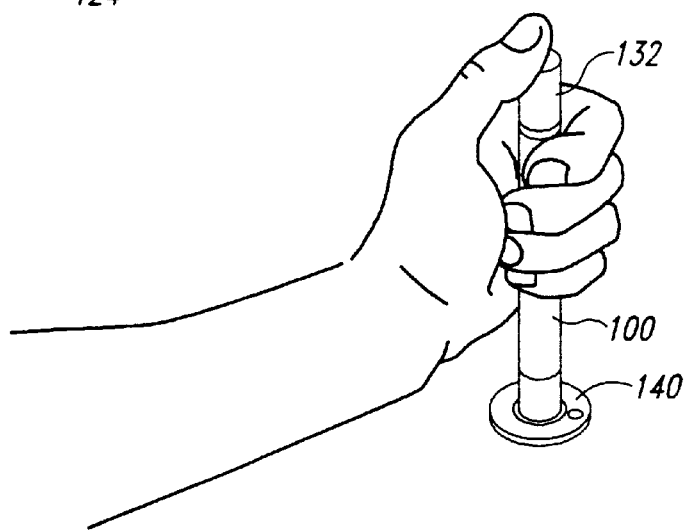
FIG. 6 is an elevational view showing the introducer of FIG. 1 in the process of deploying an electrode.
Figure 7:
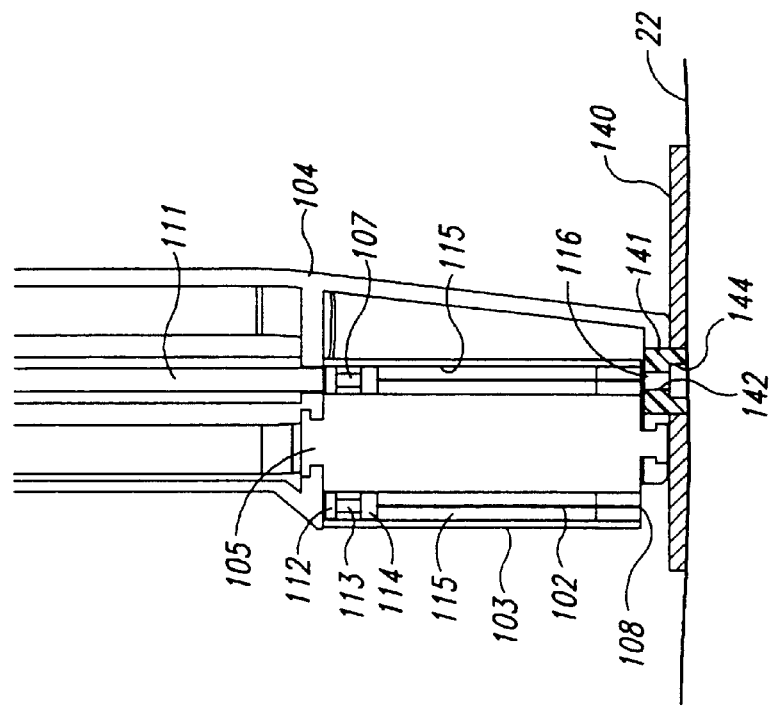
FIG. 7 is a sectional view showing the introducer of FIG. 1 in the process of deploying an electrode, prior to insertion of the electrode.

After the patch 140 is in place, the distal end of introducer 100 is placed against patch 140 so that introducer aperture 117 surrounds the upwardly extending portion of rigid patch member 141, as shown in FIG. 6. This interaction aligns the opening 116 of one of the introducer's magazine chambers 115 with the opening 142 of rigid member 141 and helps control the electrode's angle of entry, as shown in FIG. 7. The line-of-sight action of the introducer (i.e., the electrode moves along, or parallel to, the introducer's longitudinal axis) helps in the accurate placement of the electrodes.

Downward pressure on introducer 100 compresses patch 140, thereby causing the upper surface of rigid member 141 to engage a lower surface of magazine 103 and pressing rigid member 141 downward into the patient's skin 22. This pressure on the patient's skin around the insertion site minimizes the pain of insertion of the electrode. The amount of downward pressure applied during insertion can be controlled by responding upward forces from the user's hand holding the introducer. If desired, the heel of the user's hand holding the introducer can rest against the patient adjacent the insertion site to steady the introducer.

Depressing actuator 132 moves gear rack 130 distally, which causes gears 128 and 122 to rotate. Because of the relative diameters and relative tooth counts of gears 128 and 122, gear rack 120 moves longitudinally a much greater distance than the corresponding longitudinal movement of gear rack 130. This feature enables the electrode to be inserted its required distance into the patient's skin using only a comparatively small movement of the operator's thumb. Distal movement of gear rack 120 is guided by the movement of slide member 109 along rail 110.

Figure 8:
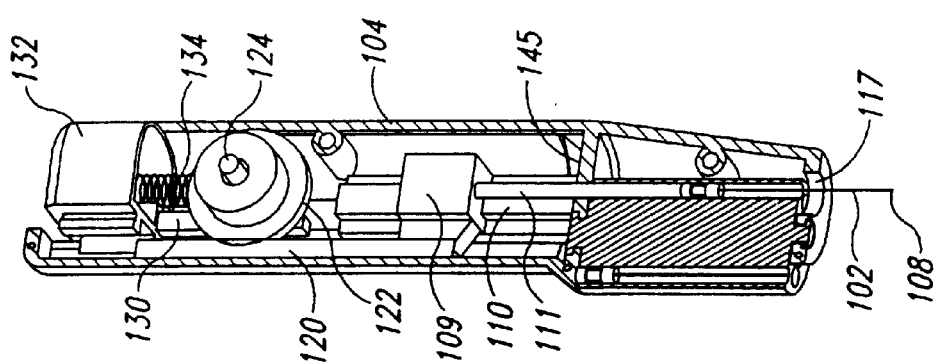
FIG. 8 is a sectional view showing the introducer of FIG. 1 in the process of deploying an electrode, during insertion of the electrode.

As slide member 109 moves distally, drive rod 111 moves into a magazine chamber 115 until the distal end of drive rod 111 engages the top surface of the electrode's handle portion 107. As shown in FIG. 8, further distal movement of drive rod 111 pushes electrode 102 downward so that sharp point 108 of electrode 102 leaves the introducer housing and enters the patient's skin 22 and the tissue beneath the skin. Chamber 115 provides axial stability to the electrode 102 during insertion.

When the top portion 112 of electrode handle portion 107 leaves the smaller diameter portion 118 of magazine chamber 115, it enters the larger diameter portion 119 of chamber 115. At this point (shown in FIG. 9), because the diameter of chamber portion 119 is wider than the diameter of the electrode handle 107, the electrode is no longer attached to introducer 100.

Continued downward movement of actuator 132 and drive rod 111 pushes the lower larger diameter portion 114 of electrode handle 107 through the smaller diameter portion 142 of rigid member 141 by compressing handle portion 114. Further downward movement pushes handle portion 114 into the larger diameter portion 144 of rigid member 141 so that the rigid member's smaller diameter portion lies between the larger diameter portions 112 and 114 of the electrode handle 107. This interaction holds the electrode in place in the patient's tissue and helps provides depth control for electrode insertion. In this embodiment, the preferred depth of the electrode's sharp point 108 is approximately 3 cm., although other electrode depths may be desired depending on the treatment to be performed. Slider member 109 also acts as a limit stop at this point when it engages the limit stop area 145 of housing 104, thereby also controlling electrode insertion depth.

Actuator 132 and electrode 102 move in the same direction during insertion: along, or parallel to, the longitudinal axis of the introducer. This common directional movement, along with the ergonomic design of the introducer allowing it to be held and operated by one hand, helps control electrode insertion speed and pressure on the patient.

Figure 10:
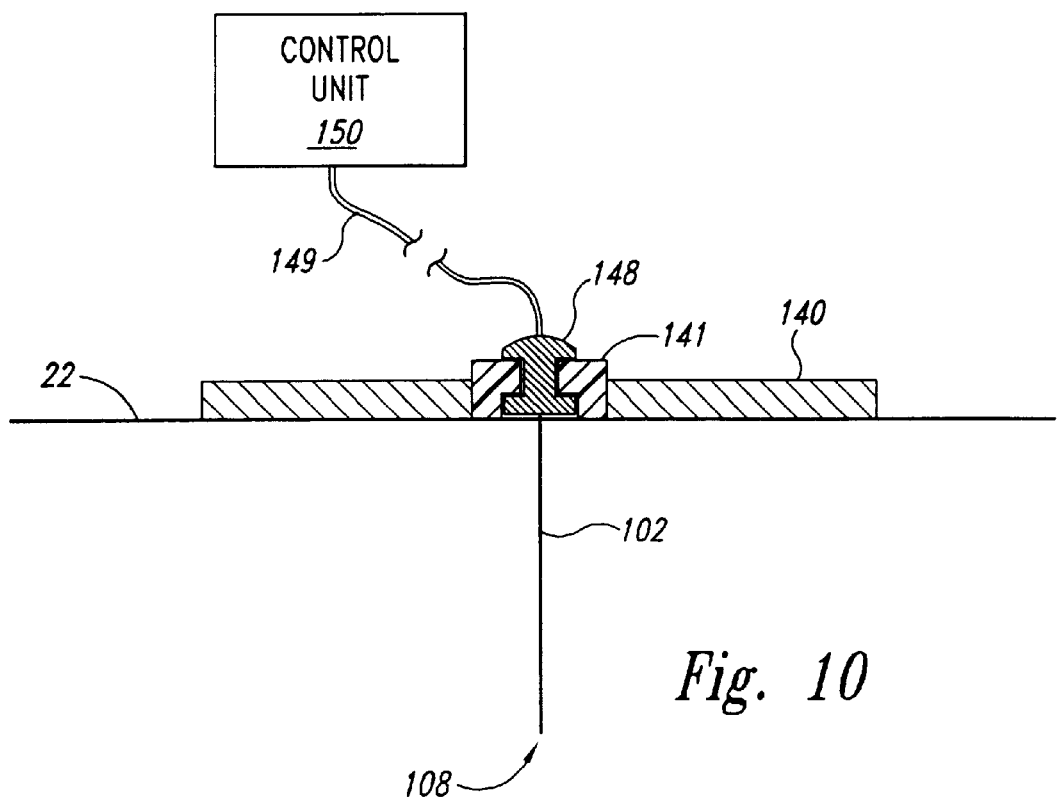
FIG. 10 is a sectional view of an inserted electrode assembly of the embodiment of FIGS. 1–4.

Magazine 103 is rotated to a new insertion position and placed against an empty patch 140 after insertion of each electrode until all electrodes have been deployed and inserted. A suitable electrical connector 148 such as an alligator clip is electrically connected to electrode 102 through an aperture (not shown) formed in the upper larger diameter portion 112 of electrode handle 107 to provide electrical communication between a control unit 150 and electrode 102 via a cable or other conductor 149, as shown in FIG. 10. Patch 140 provides strain relief for electrode 102 by preventing tugging forces on cable 149 from dislodging the electrode from the patient, thereby helping keep the electrode in place.

Control unit 150 supplies stimulation current to the electrodes, e.g., in the manner described in the Ghoname et al. articles. Once again, the electrical waveform provided by the control unit depends on the application. For example, in an embodiment of a system providing percutaneous neuromodulation therapy, control unit 150 would preferably provide a current-regulated and current-balanced waveform with an amplitude of up to approximately 20 mA, frequency between approximately 4 Hz and 50 Hz, and pulse width of between approximately 50 $\mu$sec and 1 msec.

It should be noted that at no time during the electrode deployment, insertion and electrical therapy treatment processes was the sharp point of the electrode exposed to the operator or bystanders.

In an alternative embodiment, the lower wide portion of the electrode handle is formed from a rigid material and has rounded camming edges. The central annulus of patch 140 in this alternative embodiment is either compressible or has a resilient camming opening under the camming action of the electrode handle.

Modifications of the above embodiments of the invention will be apparent to those skilled in the art. For example, while the invention was described in the context of percutaneous electrical therapy in which electrodes are used to deliver electricity to a patient, the introducer may be used with electrodes designed for medical monitoring and/or diagnosis. In addition, the introducer of this invention may be used with acupuncture needles or other needles not used for conducting electricity to or from a patient.

What is claimed is:

1. A percutaneous electrode introducer comprising:
   a housing configured to be held in a user's hand, the housing comprising an aperture at a distal end;
   a plurality of electrodes disposed in the housing, the electrodes comprising a sharp point at a distal end; and
   an actuator configured to be operable by a user to move each of the electrode individually through the aperture and completely out of the housing to place the sharp point of each of the electrodes beneath a patient's skin.

2. The introducer of claim 1 further comprising a magazine in which the plurality of electrodes is disposed.

3. The introducer of claim 2 wherein the magazine comprises a plurality of electrode chambers.

4. A percutaneous electrode introducer comprising:
   a housing configured to be held in a user's hand, the housing comprising an aperture at a distal end;
   an electrode disposed in the housing, the electrode comprising a sharp point at a distal end; and
   an actuator adapted to be operable by a user to move the electrode through the aperture and completely out of the housing to place the sharp point of the electrode beneath a patient's skin;
   wherein the aperture is configured to cooperate with an alignment element to align the introducer with an electrode insertion site.

5. The introducer of claim 4 wherein the electrode comprises an electrical connector portion at a proximal end, the actuator being further configured to place the sharp point of the electrode beneath the patient's skin with the electrical connector portion of the electrode being exposed above the patient's skin.

6. The introducer of claim 4 wherein the actuator is further configured to be operated by a user's thumb to move the electrode through the aperture.

7. The introducer of claim 4 wherein the actuator and electrode are configured to move in the same direction during placement of the sharp point of the electrode beneath the patient's skin.

8. The introducer of claim 4 wherein the introducer has a longitudinal axis, the actuator and the electrode being configured to move along, or parallel to, the longitudinal axis during placement of the sharp point of the electrode beneath the patient's skin.

9. A percutaneous electrode introducer comprising:
   a housing configured to be held in a user's hand, the housing comprising an aperture at a distal end;
   an electrode disposed in the housing, the electrode comprising a sharp point at a distal end;
   an actuator configured to be operable by a user to move the electrode through the aperture and completely out of the housing to place the sharp point of the electrode beneath a patient's skin; and
   a transmission assembly configured to move the electrode's sharp point a first distance when the actuator is moved a second distance, the second distance being less than the first distance;
   wherein the introducer has a longitudinal axis, the actuator and the electrode being configured to move along, or parallel to, the longitudinal axis during placement of the sharp point of the electrode beneath the patient's skin.

* * * * *

UNITED STATES PATENT AND TRADEMARK OFFICE
CERTIFICATE OF CORRECTION

PATENT NO.     : 6,556,869 B1
DATED          : April 29, 2003
INVENTOR(S)    : Leonard et al.

It is certified that error appears in the above-identified patent and that said Letters Patent is hereby corrected as shown below:

Column 6,
Line 2, "electrode" should be -- electrodes --;
Lines 28 and 35, "patient' skin" should be -- patient's skin --;

Signed and Sealed this

First Day of July, 2003

JAMES E. ROGAN
*Director of the United States Patent and Trademark Office*